United States Patent [19]

Halverson et al.

[11] Patent Number: 4,975,027

[45] Date of Patent: Dec. 4, 1990

[54] EXTREME PRESSURE FLUID SAMPLE TRANSFER PUMP

[75] Inventors: Justin E. Halverson, Grovertown, Ga.; Wilfred W. Bowman, North Augusta, S.C.

[73] Assignee: The United States of America as represented by the United States Department of Energy, Washington, D.C.

[21] Appl. No.: 362,993

[22] Filed: Jun. 8, 1989

[51] Int. Cl.$^5$ .............................................. F04B 37/12
[52] U.S. Cl. ..................................... 417/392; 417/437
[58] Field of Search ............... 417/392, 414, 437, 439; 73/864.5; 92/36

[56] References Cited

U.S. PATENT DOCUMENTS

| | | | |
|---|---|---|---|
| 1,891,771 | 12/1932 | Mendenhall et al. | 417/414 |
| 3,285,191 | 11/1966 | Taplin | 417/439 |
| 3,635,092 | 1/1972 | Maughan et al. | 73/421.5 |
| 3,640,082 | 2/1972 | Dehne | 417/439 |
| 3,866,474 | 2/1975 | Hasselman | 73/421.5 |
| 4,459,865 | 7/1984 | Welker | 73/864.62 |
| 4,463,599 | 8/1984 | Welker | 73/61.1 |
| 4,463,603 | 8/1984 | Welker | 73/168 |
| 4,515,530 | 5/1985 | Christoleit | 417/214 |
| 4,556,369 | 12/1985 | Braun | 417/437 |
| 4,635,487 | 1/1987 | Gowing | 73/864.62 |
| 4,781,544 | 11/1988 | Leonard et al. | 417/392 |

Primary Examiner—Leonard E. Smith
Assistant Examiner—Robert N. Blackmon
Attorney, Agent, or Firm—Stephen D. Hamel; William R. Moser; Richard E. Constant

[57] ABSTRACT

A transfer pump for samples of fluids at very low or very high pressures comprising a cylinder having a piston sealed with an O-ring, the piston defining forward and back chambers, an inlet and exit port and valve arrangement for the fluid to enter and leave the forward chamber, and a port and valve arrangement in the back chamber for adjusting the pressure across the piston so that the pressure differential across the piston is essentially zero and approximately equal to the pressure of the fluid so that the O-ring seals against leakage of the fluid and the piston can be easily moved, regardless of the pressure of the fluid. The piston may be actuated by a means external to the cylinder with a piston rod extending through a hole in the cylinder sealed with a bellows attached to the piston head and the interior of the back chamber.

19 Claims, 3 Drawing Sheets

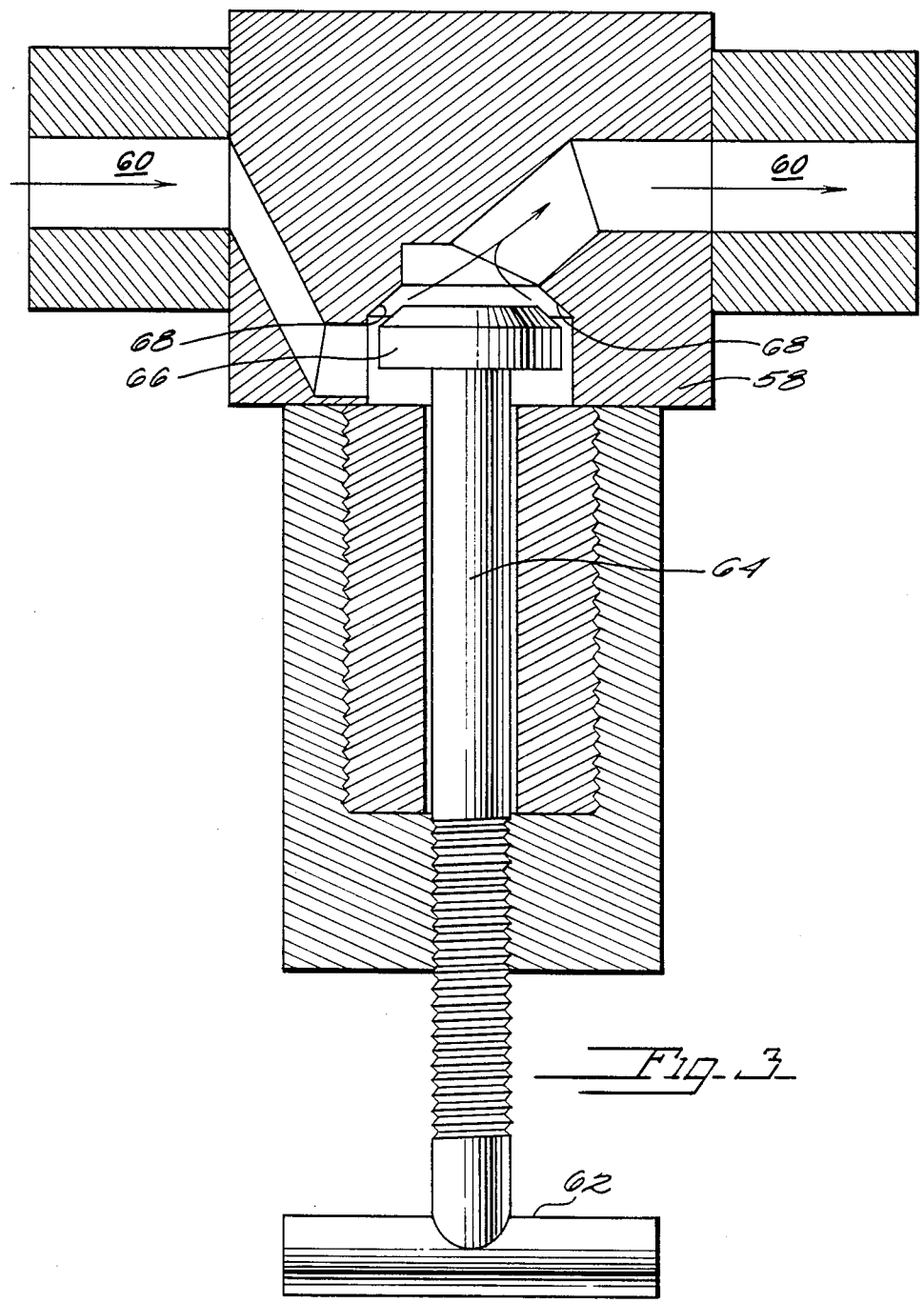

EXTREME PRESSURE FLUID SAMPLE TRANSFER PUMP

BACKGROUND OF THE INVENTION

1. Field of the Invention and Contract Statement

The present invention relates to sample transfer pumps and in particular to pumps for sampling fluids at very small or very large pressures. The United States Government has rights in this invention pursuant to Contract No. DE-AC09-76SR00001 between the U.S. Department of Energy and E. I. DuPont de Nemours & Co.

2. Discussion of Background

There are a variety of fluid sample transfer pumps and, indeed, pumps of all sorts are well known. For sampling fluids at very large or very small pressures, typically a bladder is placed in an over-container which is evacuated to cause the sample to be drawn into the bladder. To expell the sample from the bladder, the over-container is refilled thereby expressing the sample from the bladder. See for example, the devices disclosed in U.S. Pat. No. 4,635,487 and 3,806,474.

Although pistons are efficient pumps, they are difficult to seal when the pressure differential across the piston is too great. Mechanical seals are used if standard O-rings will not hold the seal. A mechanical seal for sealing the edge of a moving piston against a cylinder wall presents significant, obvious design conflicts.

For very low pressures, the Toeppler pump has been used to transfer samples of gases in a high vacuum system. The Toeppler pump uses a reservoir of mercury to pump a gas from one container to another and can reduce the pressure in the container down to about $10^{-5}$ Torr. The Toeppler pump, even when automatically operated, is slow in moving a significant volume of gas.

SUMMARY OF THE INVENTION

To overcome the problems and disadvantages of other sample transfer pumps, the invention comprises a cylinder with a piston therein dividing the cylinder into a forward chamber and a back chamber. The piston, sealed with a simple O-ring of some appropriately resilient and slidable material, is actuated to draw a first fluid into and expell the first fluid from the forward chamber. By connecting the back chamber to another pump, the pressure of the second fluid in the back chamber can be adjusted to match the pressure in the forward chamber so that the O-ring holds the seal regardless of the pressure of the first fluid.

If the piston is actuated by a piston rod extending through a hole in the cylinder to an external actuating mechanism, then a pressure boundary, such as a bellows surrounding the piston rod and connected to the cylinder and the piston, is used to create a leak-free barrier between the back chamber and the exterior of the cylinder.

It is a feature of the present invention that by adjusting the pressure behind the piston, a simple O-ring can effectively seal the piston as it transfers fluids at very high or very low pressures for sampling. It is an advantage of the present invention that, by allowing the use of a piston to transfer fluids at very low or very high pressures, such fluids can be transferred more efficiently and more quickly. Other features and advantages inherent in the invention will be apparent to those skilled in the art.

Reference is now made in detail to the present preferred embodiment of the invention, an example of which is given in the accompanying drawings.

A BRIEF DESCRIPTION OF THE DRAWINGS

The accompanying drawings, which are incorporated in and form a part of the specification, illustrate the invention, and, together with the description, serve to explain the principles of the invention. In the drawings;

FIG. 3 is a detailed, side, cross-sectional view of one of the valves.

DETAILED DESCRIPTION OF THE INVENTION

Figure 1:
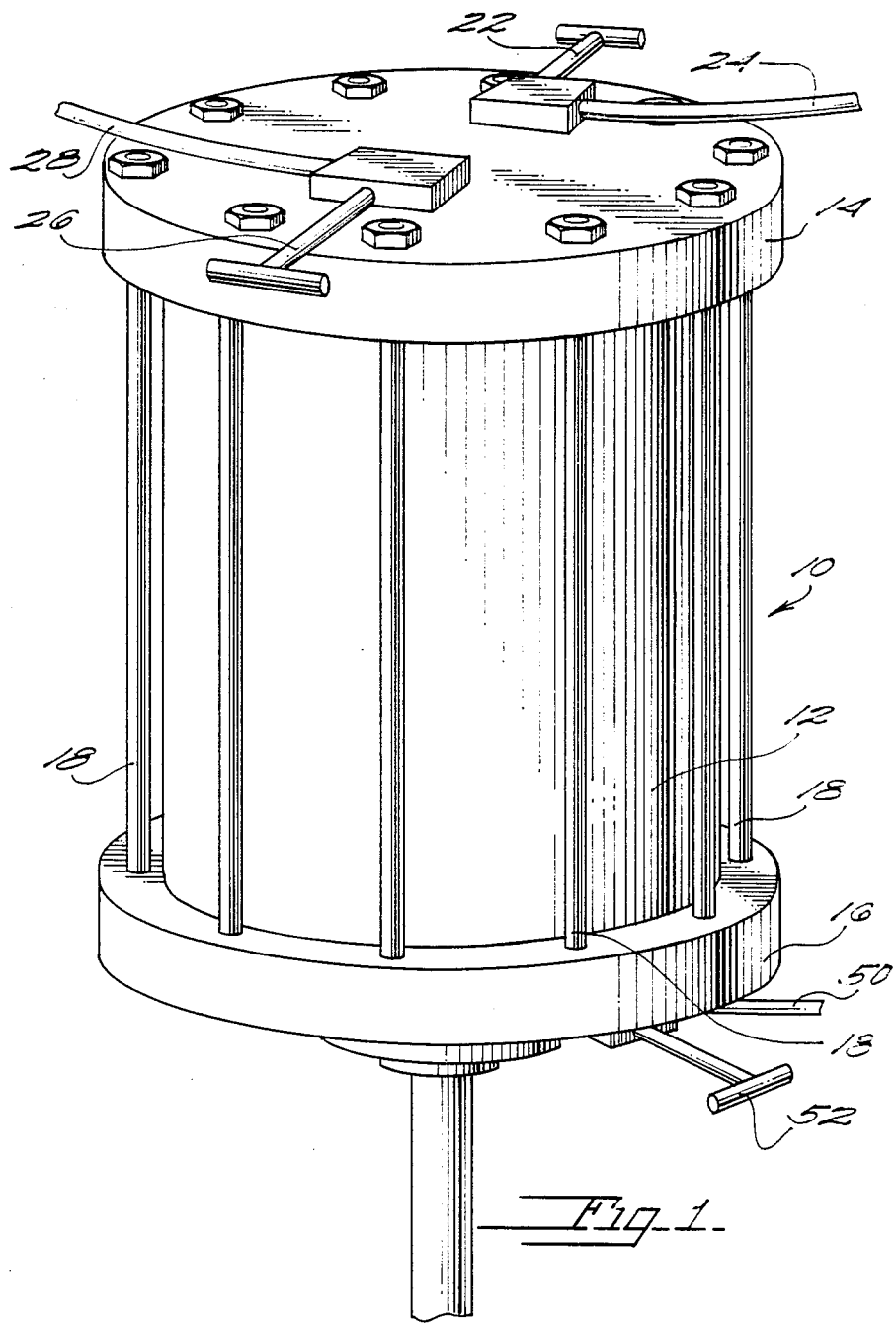
FIG. 1 is a perspective view of the present invention.

Referring now to FIG. 1, a transfer pump, indicated generally at 10 comprises a cylinder 12, a top 14 and a bottom 16. Top 14 and bottom 16 are held firmly in place against the ends of cylinder 12 by a plurality of bolts 18. An inlet valve 22 controls the flow of a fluid though inlet pipe 24; an exit valve 26 controls the flow of the fluid through exit pipe 28 At the bottom of transfer pump 10, a portion of a piston rod 32 is shown extending externally of pump 10.

Figure 2:
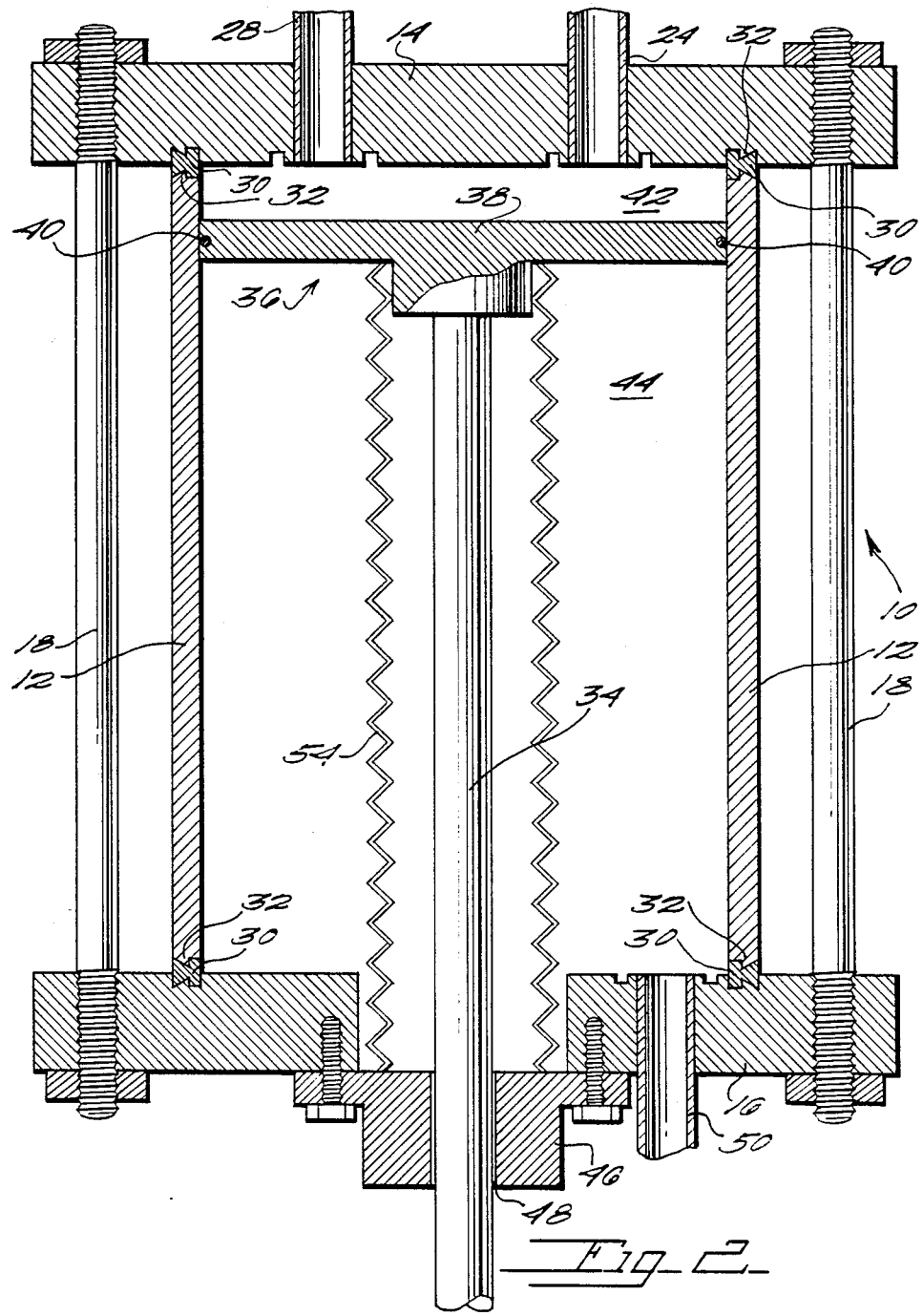
FIG. 2 is a side, cross-sectional view according to the present invention.

FIG. 2 is a cross-sectional side view of pump 10, with cylindrical wall 12, top 14, bottom 16, and bolts 18. Cylinder 12 and top 14 and bottom 16 are sealed by a metal gasket 20, such as a copper gasket, between conflat flanges 34. Inlet pipe 24 and exit pipe 28 are welded to top 14. Inside cylinder 12 is a piston 36 with a piston head 38 and piston rod 32 attached to piston head 38. Piston head 38 is sealed against the interior of cylinder 12 by an O-ring 40. As piston rod 32 is actuated, piston 36 moves up and down, its top stroke defining the minimum volume of cylinder 12, its bottom stroke defining the maximum volume of cylinder 12. Above piston head 38 is a forward chamber 42; behind piston head 38 is a back chamber 44. The fluids in the forward chamber and back chamber may be the same or different depending on the application.

Piston rod 32 extends to a flanged base 46 in bottom 16, then through a hole 48.

An additional pipe 50 is located in bottom 16 for connection with a vacuum pump or pressure pump (not shown) depending on whether the fluid to be transferred is at high or low pressure. A back chamber valve 52 (see FIG. 1) controls the flow of the fluid through pipe 50.

To seal back chamber 44 against leakage through hole 48 when piston rod 34 is actuated by a means external to pump 10, a bellows 54 is attached to piston head 38 and bottom 16, preferably at flanged base 46 for maintenance. Bellows 54 compresses and extends as piston 36 moves from top stroke to bottom stroke and back without otherwise interfering with the operation of piston 36. Bellows 54 is preferably made of metal or equivalent material impermiable to the fluid of back chamber 44.

FIG. 3 shows a typical valve 56 for use as inlet valve 22, exit valve 26 or back chamber valve 52. The valve has a body 58 having a flow path 60 that can be blocked to close valve 56 by turning handle 62 to advance a threaded shaft 64 forward until shaft head 66 seats against surface 68 to close off flow path 60. Alternative arrangements known to those skilled in the art for stopping the flow of a fluid at high or low pressures in a pipe could be substituted.

In use, pump 10 is operated as follows: Inlet valve 22 is closed and foreward and back chambers 42, 42 are pressurized to operating pressure, approximately that of the fluid to be transferred. Piston 36 is moved to the top stroke. With exit and back chamber valves 26, 52 closed, inlet valve 22 is opened and piston 36 moved to bottom stroke. Inlet valve 22 is closed; exit valve 26 is opened and piston 36 moved to top stroke, expressing the fluid from forward chamber 42. Exit valve 26 is closed and the process repeated.

The pump of the present invention can efficiently transfer minute quantities of fluids (other than the residual fluid in the volume represented by the inlet and exit lines) at low pressure without contaminating other than the forward chamber and inlet and exit lines because of the combination of the evacuation of the back chamber and the piston sealed with an O-ring. Fluids at pressures down to $10^{-8}$ Torr can be transferred versus a limit of $10^{-5}$ Torr with the Toeppler pump. The piston and valve sequence can be automated to take place quickly. Alternatively, fluids at very high pressures can also be transferred using the piston/O-ring arrangement when hack chamber 44 is pressurized to match the pressure of foreward chamber 42.

The foregoing description of preferred embodiments of the invention has been presented for purposes of illustration and description. It is not intended to be exhaustive or to limit the invention to the precise form disclosed, and obviously many modifications and variations are possible in light of the above teachings. The embodiments were chosen and described in order to best explain the principles of the invention and its practical application to thereby enable one skilled in the art to best utilize the invention in various embodiments and with various modifications as are suited to the particular use contemplated. It is intended that the scope of the invention be defined by the claims appended hereto.

What is claimed is:

1. An apparatus for pumping a first fluid comprising:
   a cylinder;
   a piston positioned within said cylinder and dividing said cylinder into a forward chamber and a back chamber;
   a second fluid in said back chamber;
   a means for actuating said piston;
   a means for sealing said piston against the interior of said cylinder; and
   a means for adjusting the pressure of said second fluid in said back chamber so that the pressure of said first fluid and said second fluid are approximately equal, said forward chamber isolated from said back chamber so that said first fluid does not mix with said second fluid.

2. The pump of claim 1 further comprising first conduit means for conducting said first fluid into and out of said forward chamber and valve means for controlling the flow of said fluid through said conduit means.

3. The pump of claim 1 wherein said adjusting means further comprises a back chamber valve for controlling the flow of said second fluid into and out of said back chamber, a second conduit means for conducting said second fluid into and out of said back chamber, and a means for pumping said second fluid into and out of said back chamber.

4. The pump of claim 2 wherein said adjusting means further comprises a back chamber valve for controlling the flow of said second fluid into and out of said back chamber, a second conduit means for conducting said second fluid into and out of said back chamber, and a means for pumping said second fluid into and out of said back chamber.

5. The pump of claim 1 wherein said actuating means is external to said cylinder and in operative connection with said piston.

6. The pump of claim 2 wherein said actuating means is external to said cylinder and in operative connection with said piston.

7. The pump of claim 3 wherein said actuating means is external to said cylinder and in operative connection with said piston.

8. The pump of claim 4 wherein said actuating means is external to said cylinder and in operative connection with said piston.

9. The pump of claim 1 wherein said cylinder has a hole in said back chamber and said piston further comprises a piston head and a piston rod attached to said piston head, said piston rod slidably extending through said hole to said actuating means external to said cylinder, said piston having a means for sealing said hole.

10. The pump of claim 2 wherein said cylinder has a hole in said back chamber and said piston further comprises a piston head and a piston rod attached to said piston head, said piston rod extending through said hole to said actuating means external to said cylinder, said piston having a means for sealing said hole.

11. The pump of claim 3 wherein said cylinder has a hole in said back chamber and said piston further comprises a piston head and a piston rod attached to said piston head, said piston rod extending through said hole to said actuating means external to said cylinder, said piston having a means for sealing said hole.

12. The pump of claim 4 wherein said cylinder has a hole in said back chamber and said piston further comprises a piston head and a piston rod attached to said piston head, said piston rod extending through said hole to said actuating means external to said cylinder, said piston having a means for sealing said hole.

13. An apparatus for pumping a first fluid comprising:
   a cylinder having a hole;
   a piston head positioned within said chamber and dividing said cylinder into a forward chamber and a back chamber;
   a second fluid in said back chamber;
   a piston rod attached to said piston head, said piston rod extendeing through said hole in said cylinder;
   a means exterior to said cylinder for actuating said piston rod so that said piston head slides within said cylinder;
   an O-ring carried by said piston for slidably sealing said piston against the interior of said cylinder;
   first conduit means for conducting said first fluid into and out of said forward chamber;
   valve means for controlling the flow of said first fluid through said first conduit means;
   a means for sealing said piston head to said cylinder so that said second fluid does not leak through said hole in said cylinder as said piston rod is actuated; and
   a means for adjusting the pressure of said second fluid in said back chamber in operative connection with said back chamber, said forward chamber isolated from said back chamber so that said first fluid does not mix with said second fluid.

14. The apparatus of claim 13 wherein said adjusting means further comprises:
a second conduit means for conducting said second fluid into and out of said back chamber;
second valve means for controlling the flow of said second fluid through said conduit means; and
a pump for pumping said second fluid into and out of said back chamber through said second conduit means.

15. The apparatus of claim 13 wherein said sealing means comprises a bellows attached to said piston head and said back chamber, said bellows compressing and extending as said piston is actuated.

16. The apparatus of claim 14 wherein said sealing means comprises a bellows attached to said piston head and said back chamber, said bellows compressing and extending as said piston is actuated.

17. The apparatus of claim 15 wherein said valve means further comprises an inlet valve and an exit valve, and said first conduit means comprises an inlet pipe in communication with said forward chamber and an exit pipe in communication with said forward chamber, said inlet valve connected to said inlet pipe and said exit valve connected to said exit pipe.

18. The apparatus of claim 16 wherein said valve means further comprises an inlet valve and an exit valve, and said first conduit means comprises an inlet pipe in communication with said forward chamber and an exit pipe in communication with said forward chamber, said inlet valve connected to said inlet pipe and said exit valve connected to said exit pipe.

19. A method for transferring a sample of a first fluid from a first container to a second container using a piston in cylinder having a second fluid isolated from said first fluid, said piston having a top stroke and a bottom stroke, said top stroke defining a minimum volume of said cylinder and said bottom stroke defining a maximum volume of said cylinder, said method comprising the steps of:
isolating said cylinder from said fluid;
adjusting the pressure of said second fluid in the cylinder to match the pressure of said first fluid;
moving said piston to said top stroke;
allowing said first fluid to enter said chamber from said first container;
moving said piston to said bottom stroke;
isolating said cylinder from said first container;
allowing said first fluid to leave said cylinder and enter said second container; and
moving said piston to said top stroke.

* * * * *